United States Patent
Gaeckle et al.

(10) Patent No.: US 7,883,520 B2
(45) Date of Patent: Feb. 8, 2011

(54) CORNEAL EPITHELIAL POCKET FORMATION SYSTEMS, COMPONENTS AND METHODS

(75) Inventors: Markus Gaeckle, Bad Liebenzell (DE); Helmut Maas, Bad Liebenzell (DE); Daniel Wolf, Stuttgart (DE); Tanja Riehl, Pflorzheim (DE)

(73) Assignee: ForSight Labs, LLC, Menlo Park, CA (US)

( * ) Notice: Subject to any disclaimer, the term of this patent is extended or adjusted under 35 U.S.C. 154(b) by 600 days.

(21) Appl. No.: 11/693,624

(22) Filed: Mar. 29, 2007

(65) Prior Publication Data
US 2007/0239184 A1    Oct. 11, 2007

Related U.S. Application Data

(60) Provisional application No. 60/790,874, filed on Apr. 10, 2006.

(51) Int. Cl.
*A61F 9/00* (2006.01)
(52) U.S. Cl. .................... 606/166; 606/170
(58) Field of Classification Search ............. 606/166, 606/167, 169–172
See application file for complete search history.

(56) References Cited

U.S. PATENT DOCUMENTS

| | | | |
|---|---|---|---|
| 4,078,564 A | 3/1978 | Spina et al. | |
| 4,126,904 A | 11/1978 | Shepard | |
| 4,223,984 A | 9/1980 | Miyata et al. | |

(Continued)

FOREIGN PATENT DOCUMENTS

CA          2134744          5/1995

(Continued)

OTHER PUBLICATIONS

"Licensing agreement for automated microkeratome-based device" found online at: http://www.optical-world.co.uk/Aug%202002%20international_outlook.htm. no author given, printed on Sep. 13, 2002.

(Continued)

*Primary Examiner*—Ahmed M Farah
(74) *Attorney, Agent, or Firm*—Townsend and Townsend and Crew LLP

(57) ABSTRACT

Corneal epithelial pocket formation systems include a cutting head and a blade coupled to the cutting head. The blade is coupled to the cutting head at an orientation that is effective in maintaining a viable separated pocket defining portion of corneal epithelium of an eye of a patient during formation of a corneal epithelial pocket of the eye. The blade includes a cutting edge surface at its distal end. The cutting edge surface is effective in separating the corneal epithelium from the underlying Bowman's membrane of the eye without leaving residual corneal epithelial cells in contact with Bowman's membrane that may result in corneal epithelial cell growth between a corneal implant located in the corneal epithelial pocket and the underlying Bowman's membrane. Versions of the present systems include spring loaded blade holders, which may be removable from the cutting head. Versions also can include applanators. Packages containing spring loaded blade holders and blades, and disposable blades useful with the present systems are also described. The components, including disposable components, can be used to produce the present systems, and the present systems and components can be used in methods of enhancing or correcting a patient's vision.

17 Claims, 4 Drawing Sheets

U.S. PATENT DOCUMENTS

| | | | |
|---|---|---|---|
| 4,268,131 A | 5/1981 | Miyata et al. | |
| 4,346,482 A | 8/1982 | Tennant et al. | |
| 4,452,235 A | 6/1984 | Reynolds | |
| 4,452,776 A | 6/1984 | Refojo | |
| 4,452,925 A | 6/1984 | Kuzma et al. | |
| 4,563,779 A | 1/1986 | Kelman | |
| 4,581,030 A | 4/1986 | Bruns et al. | |
| 4,600,533 A | 7/1986 | Chu | |
| 4,619,657 A | 10/1986 | Keates et al. | |
| 4,621,912 A | 11/1986 | Meyer | |
| 4,624,669 A | 11/1986 | Grendahl | |
| 4,636,210 A | 1/1987 | Hoffer | |
| 4,655,774 A | 4/1987 | Choyce | |
| 4,655,980 A | 4/1987 | Chu | |
| 4,676,790 A | 6/1987 | Kern | |
| 4,689,399 A | 8/1987 | Chu | |
| 4,693,715 A | 9/1987 | Abel, Jr. | |
| 4,715,858 A | 12/1987 | Lindstrom | |
| 4,725,671 A | 2/1988 | Chu et al. | |
| 4,780,409 A | 10/1988 | Monji et al. | |
| 4,784,485 A | 11/1988 | Ho | |
| 4,799,931 A | 1/1989 | Lindstrom | |
| 4,810,082 A | 3/1989 | Abel, Jr. | |
| 4,819,617 A | 4/1989 | Goldberg et al. | |
| 4,834,748 A | 5/1989 | McDonald | |
| 4,851,003 A | 7/1989 | Lindstrom | |
| 4,923,467 A | 5/1990 | Thompson | |
| 4,952,212 A | 8/1990 | Booth et al. | |
| 4,959,353 A | 9/1990 | Brown et al. | |
| 4,973,493 A | 11/1990 | Guire | |
| 4,978,713 A | 12/1990 | Goldenberg | |
| 4,979,959 A | 12/1990 | Guire | |
| 4,981,841 A | 1/1991 | Gibson | |
| 4,983,181 A | 1/1991 | Civerchia | |
| 4,994,081 A | 2/1991 | Civerchia | |
| 5,019,097 A | 5/1991 | Knight et al. | |
| 5,044,743 A | 9/1991 | Ting | |
| 5,104,408 A | 4/1992 | Thompson | |
| 5,108,428 A | 4/1992 | Capecchi et al. | |
| 5,112,350 A | 5/1992 | Civerchia | |
| 5,114,627 A | 5/1992 | Civerchia | |
| 5,151,310 A | 9/1992 | Yanagisawa et al. | |
| 5,156,622 A | 10/1992 | Thompson | |
| 5,163,956 A | 11/1992 | Liu et al. | |
| 5,171,318 A | 12/1992 | Gibson et al. | |
| 5,192,316 A | 3/1993 | Ting | |
| 5,196,026 A | 3/1993 | Barrett et al. | |
| 5,196,027 A | 3/1993 | Thompson et al. | |
| 5,201,764 A | 4/1993 | Kelman et al. | |
| 5,213,720 A | 5/1993 | Civerchia | |
| 5,244,799 A | 9/1993 | Anderson | |
| 5,263,992 A | 11/1993 | Guire | |
| 5,288,436 A | 2/1994 | Liu et al. | |
| 5,292,514 A | 3/1994 | Capecchi et al. | |
| 5,300,118 A | 4/1994 | Silvestrini et al. | |
| 5,330,911 A | 7/1994 | Hubbell et al. | |
| 5,401,508 A | 3/1995 | Manesis | |
| 5,433,745 A | 7/1995 | Graham et al. | |
| 5,443,473 A | 8/1995 | Miller et al. | |
| 5,470,831 A | 11/1995 | Whitman et al. | |
| 5,475,052 A | 12/1995 | Rhee et al. | |
| 5,489,300 A | 2/1996 | Capecchi et al. | |
| 5,496,339 A | 3/1996 | Koepnick | |
| 5,522,888 A | 6/1996 | Civerchia | |
| 5,547,468 A | 8/1996 | Simon et al. | |
| 5,552,452 A | 9/1996 | Khadem et al. | |
| 5,565,519 A | 10/1996 | Rhee et al. | |
| 5,587,175 A | 12/1996 | Viegas et al. | |
| 5,614,587 A | 3/1997 | Rhee et al. | |
| 5,632,773 A | 5/1997 | Graham et al. | |
| 5,683,592 A * | 11/1997 | Bartholomew et al. ........ 216/24 | |
| 5,690,657 A | 11/1997 | Koepnick | |
| 5,713,957 A | 2/1998 | Steele et al. | |
| 5,716,633 A | 2/1998 | Civerchia | |
| 5,722,971 A | 3/1998 | Peyman | |
| 5,744,545 A | 4/1998 | Rhee et al. | |
| 5,800,541 A | 9/1998 | Rhee et al. | |
| 5,827,641 A | 10/1998 | Parenteau et al. | |
| 5,832,313 A | 11/1998 | Ishibashi et al. | |
| 5,836,313 A | 11/1998 | Perez et al. | |
| 5,919,185 A | 7/1999 | Peyman | |
| 5,964,748 A | 10/1999 | Peyman | |
| 5,994,133 A | 11/1999 | Meijs et al. | |
| 6,015,609 A | 1/2000 | Chaouk et al. | |
| 6,030,634 A | 2/2000 | Wu et al. | |
| 6,055,990 A | 5/2000 | Thompson | |
| 6,060,530 A | 5/2000 | Chaouk et al. | |
| 6,063,073 A | 5/2000 | Peyman | |
| 6,071,293 A | 6/2000 | Krumeich | |
| 6,086,204 A | 7/2000 | Magnante | |
| 6,090,995 A | 7/2000 | Reich et al. | |
| 6,099,541 A * | 8/2000 | Klopotek ................... 606/166 |
| 6,103,528 A | 8/2000 | An et al. | |
| 6,165,488 A | 12/2000 | Tardy et al. | |
| 6,186,148 B1 | 2/2001 | Okada | |
| 6,197,019 B1 | 3/2001 | Peyman | |
| 6,203,538 B1 | 3/2001 | Peyman | |
| 6,217,571 B1 | 4/2001 | Peyman | |
| 6,221,067 B1 | 4/2001 | Peyman | |
| 6,271,278 B1 | 8/2001 | Park et al. | |
| 6,280,470 B1 | 8/2001 | Peyman | |
| 6,284,537 B1 | 9/2001 | Offord et al. | |
| 6,323,278 B2 | 11/2001 | Rhee et al. | |
| 6,335,006 B1 | 1/2002 | Miller et al. | |
| 6,361,560 B1 | 3/2002 | Nigam | |
| 6,384,105 B1 | 5/2002 | He et al. | |
| 6,388,047 B1 | 5/2002 | Won et al. | |
| 6,454,800 B2 | 9/2002 | Dalton et al. | |
| 6,454,802 B1 | 9/2002 | Bretton et al. | |
| 6,511,949 B1 | 1/2003 | Nitta et al. | |
| 6,544,286 B1 | 4/2003 | Perez | |
| 6,547,391 B2 | 4/2003 | Ross, III et al. | |
| 6,551,307 B2 | 4/2003 | Peyman | |
| 6,566,406 B1 | 5/2003 | Pathak et al. | |
| 6,579,918 B1 | 6/2003 | Auten et al. | |
| 6,585,375 B2 | 7/2003 | Donitzky et al. | |
| 6,596,006 B1 * | 7/2003 | Hanna ........................ 606/166 |
| 6,599,305 B1 * | 7/2003 | Feingold .................... 606/166 |
| 6,607,522 B1 | 8/2003 | Hamblin et al. | |
| 6,623,498 B1 * | 9/2003 | Ziemer ....................... 606/166 |
| 6,645,715 B1 | 11/2003 | Griffith et al. | |
| 6,689,165 B2 | 2/2004 | Jacob et al. | |
| 6,702,807 B2 | 3/2004 | Peyman | |
| 6,717,651 B2 | 4/2004 | Kato et al. | |
| 6,855,163 B2 | 2/2005 | Pallikaris et al. | |
| 6,880,558 B2 | 4/2005 | Perez | |
| 6,897,064 B2 | 5/2005 | Yoshioka et al. | |
| 6,918,904 B1 | 7/2005 | Peyman | |
| 7,004,953 B2 | 2/2006 | Pallikaris et al. | |
| 7,053,051 B2 | 5/2006 | Hendriks et al. | |
| 7,077,839 B2 | 7/2006 | Hamblin et al. | |
| 7,156,859 B2 | 1/2007 | Pallikaris et al. | |
| 7,166,118 B2 | 1/2007 | Dame et al. | |
| 7,207,998 B2 | 4/2007 | Feingold | |
| 2001/0018612 A1 | 8/2001 | Carson et al. | |
| 2001/0027314 A1 | 10/2001 | Peyman | |
| 2001/0034516 A1 | 10/2001 | Peyman | |
| 2001/0047203 A1 | 11/2001 | Dalton et al. | |
| 2002/0007217 A1 | 1/2002 | Jacob et al. | |
| 2002/0022013 A1 | 2/2002 | Leukel et al. | |
| 2002/0039788 A1 | 4/2002 | Isseroff et al. | |
| 2002/0052596 A1 | 5/2002 | Pallikaris et al. | |
| 2002/0052615 A1 | 5/2002 | Ross et al. | |
| 2002/0055753 A1 | 5/2002 | Silvestrini | |

| | | | |
|---|---|---|---|
| 2002/0065555 A1 | 5/2002 | Nigam | |
| 2002/0071097 A1 | 6/2002 | Ross, III et al. | |
| 2002/0138069 A1 | 9/2002 | Peyman | |
| 2003/0018123 A1 | 1/2003 | Bagrov et al. | |
| 2003/0018347 A1 | 1/2003 | Pallikaris et al. | |
| 2003/0018348 A1 | 1/2003 | Pallikaris et al. | |
| 2003/0093083 A1 | 5/2003 | Peyman | |
| 2003/0105521 A1 | 6/2003 | Perez | |
| 2003/0220653 A1 | 11/2003 | Perez | |
| 2004/0015234 A1 | 1/2004 | Peyman | |
| 2004/0046287 A1 | 3/2004 | Andino et al. | |
| 2004/0075807 A1 | 4/2004 | Ho et al. | |
| 2004/0125459 A1 | 7/2004 | Tanitsu et al. | |
| 2004/0142038 A1 | 7/2004 | Echols et al. | |
| 2004/0170666 A1 | 9/2004 | Keates et al. | |
| 2004/0183998 A1 | 9/2004 | Luce | |
| 2004/0243160 A1* | 12/2004 | Shiuey et al. | 606/166 |
| 2005/0070942 A1 | 3/2005 | Perez | |
| 2005/0080484 A1 | 4/2005 | Marmo et al. | |
| 2005/0124982 A1 | 6/2005 | Perez | |
| 2005/0196427 A1 | 9/2005 | Tirrell et al. | |
| 2005/0251185 A1 | 11/2005 | Gebauer | |
| 2005/0259221 A1 | 11/2005 | Marmo | |
| 2006/0034807 A1 | 2/2006 | Griffith | |
| 2006/0052796 A1 | 3/2006 | Perez et al. | |
| 2006/0064112 A1 | 3/2006 | Perez | |
| 2006/0071356 A1 | 4/2006 | Beebe | |
| 2006/0134050 A1 | 6/2006 | Griffith et al. | |
| 2006/0134170 A1 | 6/2006 | Griffith et al. | |
| 2006/0190004 A1 | 8/2006 | Dick et al. | |
| 2006/0241751 A1 | 10/2006 | Marmo et al. | |
| 2006/0246113 A1 | 11/2006 | Griffith et al. | |
| 2006/0247660 A1 | 11/2006 | Perez | |
| 2007/0016292 A1 | 1/2007 | Perez | |
| 2007/0026046 A1 | 2/2007 | Fogg et al. | |
| 2007/0182920 A1 | 8/2007 | Back et al. | |
| 2007/0265649 A1 | 11/2007 | Perez | |
| 2008/0024723 A1 | 1/2008 | Marmo | |
| 2008/0269119 A1 | 10/2008 | Griffith | |

FOREIGN PATENT DOCUMENTS

| | | |
|---|---|---|
| CA | 2286718 | 11/1998 |
| CA | 2227827 | 7/1999 |
| DE | 199 47 711 | 5/2001 |
| EP | 0 387 975 | 9/1990 |
| EP | 1 530 600 B1 | 5/2005 |
| EP | 1 741 457 A1 | 1/2007 |
| GB | 1 569 707 | 6/1980 |
| GB | 2305608 | 4/1997 |
| WO | WO 88/02622 | 4/1988 |
| WO | WO 92/14420 | 9/1992 |
| WO | WO 93/07889 | 4/1993 |
| WO | WO 94/16570 | 8/1994 |
| WO | WO 94/17851 | 8/1994 |
| WO | WO 95/13764 | 5/1995 |
| WO | WO 98/03267 | 1/1998 |
| WO | WO 98/31316 | 7/1998 |
| WO | WO 99/37752 | 7/1999 |
| WO | WO 00/07525 | 2/2000 |
| WO | WO 00/35524 | 6/2000 |
| WO | WO 00/67694 | 11/2000 |
| WO | WO 02/06883 A2 | 1/2002 |
| WO | WO 02/092142 | 11/2002 |
| WO | WO 02/092142 A3 | 11/2002 |
| WO | WO 2004/014969 | 2/2004 |
| WO | WO 2004/015090 | 2/2004 |
| WO | WO 2004/024035 | 3/2004 |
| WO | WO 2004/028356 | 4/2004 |
| WO | WO 2004/052254 A1 | 6/2004 |
| WO | WO 2005/030102 A1 | 4/2005 |
| WO | WO 2005/042043 | 5/2005 |
| WO | WO 2005/049071 A2 | 6/2005 |
| WO | WO 2005/116729 | 12/2005 |
| WO | WO 2006/007408 A1 | 1/2006 |
| WO | WO 2006/015490 | 2/2006 |
| WO | WO 2006/020859 A2 | 2/2006 |
| WO | WO 2006/116601 A2 | 11/2006 |
| WO | WO 2006/116732 A2 | 11/2006 |
| WO | WO 2007/028258 | 3/2007 |

OTHER PUBLICATIONS

Ahmed et al., "Characterization and inhibition of fibrin hydrogel-degrading enzymes during development of tissue engineering scaffolds," Tissue Eng. Jul. 2007;13(7):1469-77.

Biowski et al., "Corneal Lathing Using the Excimer Laser and a Computer-controlled Positioning System," J Refract Surg. Jan.-Feb. 2000;16(1):23-31.

Bissen-Miyajima, "At issue: the next generation of microkeratomes", Ocular Surgery news Europe! Asia.Pacific edition, Feb. 2002 , 4 pages total. Downloaded from the Internet: << http://www.osnsupersite.com/view.aspx?rid=14685>>.

Blais et al., "LBP and CD14 secreted in tears by the lacrimal glands modulate the LPS response of corneal epithelial cells," Invest Ophthalmol Vis Sci. Nov. 2005;46(11):4235-44.

Bloomfield et al., "The use of Eastman 910 monomer as an adhesive in ocular surgery. I. Biologic effects on ocular tissues," Am J Ophthalmol. Apr. 1963;55:742-748.

Bonatti et al., "A fibrin-related line of research and theoretical possibilities for the use of fibrin glue as a temporary basal membrane in non-perforated corneal ulcers and in photorefractive keratectomy (PRK)-operated corneas," Arq Bras Oftalmol. Sep.-Oct. 2007;70(5):884-889.

Bourne, "Clinical estimation of corneal endothelial pump function," Trans Am Ophthalmol Soc. 1998; 96: 229-242.

Burrill, "Gel-Assisted Lasek", Cataract & Refractive Surgery Today, no date given. 3 pages total. Downloaded from the Internet: <<http://http://www.crstodayarchive.com/03_archive/0402/crst0402_19.html>>.

Carlsson et al., "Bioengineered corneas: how close are we?" Curr Opin Ophthalmol. Aug. 2003;14(4):192-197.

Ciba Vision website, "research and development" "Sub-epithelial Separator, before year 2003", 1 page total.

Controlled Release Society Newsletter, 2005; 22(2): 1-36.

Cox, "Correcting Ocular Wavefront Aberrations using Contact Lenses", University of Bradford, downloaded from the Internet:<<http://www.brad.ac.uk/acad/lifesci/optometry/index.php/Projects/CorrectingOcular WavefrontAberrationsUsingContactLenses>>, Last modified Oct. 7, 2003.

Delustro et al., "A comparative study of the biologic and immunologic response to medical devices derived from dermal collagen," J Biomed Mater Res. Jan. 1986;20(1):109-120.

Dohlman et al., "Further experience with glued-on contact lens (artificial epithelium)," Arch Ophthalmol. Jan. 1970;83(1):10-20.

Dohlman et al., "Replacement of the corneal epithelium with a contact lens (artificial epithelium)," Trans Am Acad Ophthalmol Otolaryngol. May-Jun. 1969;73(3):482-493.

Doillon et al., "A collagen-based scaffold for a tissue engineered human cornea: physical and physiological properties," Int J Artif Organs. Aug. 2003;26(8):764-773.

Dravida et al., "A biomimetic scaffold for culturing limbal stem cells: a promising alternative for clinical transplantation," J Tissue Eng Regen Med. Jul. 2008;2(5):263-271.

Duan etal, "Biofunctionalization of collagen for improved biological response: scaffolds for corneal tissue engineering," Biomaterials. Jan. 2007;28(1): 78-88.

Engel et al., "Repair of a Traumatic Scleral Rupture With Scleral Imbrication and BioGlue," Retina. Apr.-May 2007;27(4):505-8.

EPIFIX [Brochure], Surgical Biologics, downloaded from the Internet: <<http://http://www.surgicalbio.com/pdf/surgical_biologics_epifix_brochure.pdf>>, 2 pages total.

Evans et al. "Epithelialization of a Synthetic Polymer in the Feline Cornea: a Preliminary Study," Invest. Ophthalmol. Vis. Sci. 2000, 41(7):1674-1680.

Evans et al., "A review of the development of a synthetic corneal onlay for refractive correction," Biomaterials. Dec. 2001;22(24):3319-3328.

Evans et al., "Progress in the development of a synthetic corneal onlay," Invest. Ophthalmol. Vis. Sci. 2002; 43(10): 3196-3201.

Griffith et al., "Artificial human corneas: Scaffolds for transplantation and host regeneration" Cornea. Oct. 2002;21(7 Suppl): S54-61.

Griffith et al., "Functional Human Corneal Equivalents Constructed from Cell Lines," Science Dec. 10, 1999, 286(5447):2169-2172.

Gutowska et al., "Thermosensitive Interpenetrating Polymer Networks: Synthesis. Characterization, and Macromolecular Release" Macromolecules 1994; 27(15):4167-4175.

Han et al., "A fibrin-based bioengineered ocular surface with human corneal epithelial stem cells", Cornea, 2002; 21(5):505-510.

Hicks et al., "Keratoprostheses: Advancing Toward a True Artificial Cornea" Surv Ophthalmol. Sep.-Oct. 1997;42(2):175-189.

Homolka et al., "Laser shaping of corneal transplants in vitro: area ablation with small overlapping laser spots produced by a pulsed scanning laser beam using an optimizing ablation algorithm," Phys. Med. Biol. 1999, 44:1169-1180.

Ibrahim-Elzembely, "Human fibrin tissue glue for corneal lamellar adhesion in rabbits: a preliminary study.," Cornea. Nov. 2003;22(8):735-739.

Jeong et al., "Thermosensitive sol-gel reversible hydrogels" Adv Drug Deliv Rev. Jan. 17, 2002;54(1):37-51.

Jones et al., "Silicone Hydrogel Contact Lens Materials Update—Part 1", downloaded from the Internet: <<http://www.siliconehydrogels.com/editorials/index_july.asp>>, Jul. 2004, 4 pages total.

Jones et al., "Silicone Hydrogel Contact Lens Materials Update—Part 2", downloaded from the Internet: <<http://www.siliconehydrogels.com/editorials/index_august.asp>>, Aug. 2004, 4 pages total.

Kaminski et al., "Ten-year follow-up of epikeratophakia for the correction of high myopia," Ophthalmology. Nov. 2003;110(11):2147-2152.

Kaufman et al., "Human fibrin tissue adhesive for sutureless lamellar keratoplasty and scleral patch adhesion a pilot study," Ophthalmology, 110(11): 2168-2172.

Khadem et al., "Healing of perforating rat corneal incisions closed with photodynamic laser-activated tissue glue," Lasers in surgery and medicine 2004;35(4):304-311.

Klenkler et al., "EGF-grafted PDMS surfaces in artificial cornea," Biomaterials. Dec. 2005;26(35):7286-96.

Lagali et al., "Innervation of tissue-engineered corneal implants in a porcine model: a 1-year in vivo confocal microscopy study," Invest Ophthalmol Vis Sci. Aug. 2007;48(8): 3537-3544.

Lagali et al., "Innervation of tissue-engineered recombinant human collagen-based corneal substitutes: a comparative in vivo confocal microscopy study," Invest Ophthalmol Vis Sci. Sep. 2008;49(9): 3895-902.

Latkany et al., "Plasma surface modification of artificial corneas for optimal epithelialization," J. Biomed Mater Res 1997; 36(1):29-37.

Lekskul et al., "CxGELSIX: a novel preparation of type VI collagen with possible use as a biomaterial," rnea. Mar. 2000;19(2):194-203.

Li et al., "Cellular and nerve regeneration within a biosynthetic extracellular matrix for corneal transplantation," Proc Natl Acad Sci U S A. Dec. 23, 2003;100(26): 15346-15351.

Li et al., "Recruitment of multiple cell lines by collagen-synthetic copolymer matrices in corneal regeneration," Biomaterials. Jun. 2005;26(16):3093-3104.

Liu et al., "A simple, cross-linked collagen tissue substitute for corneal implantation," Invest Ophthalmol Vis Sci. May 2006;47(5): 1869-1875.

Liu et al., "Alginate microsphere-collagen composite hydrogel for ocular drug delivery and implantation," J Mater Sci Mater Med. Nov. 2008;19(11): 3365-3371.

Liu et al., "Immunological responses in mice to full-thickness corneal grafts engineered from porcine collagen," Biomaterials Sep. 2007;28(26): 3807-3814.

Liu et al., "Properties of porcine and recombinant human collagen matrices for optically clear tissue engineering applications," Biomacromolecules. Jun. 2006;7(6):1819-1828.

Liu et al., "Recombinant human collagen for tissue engineered corneal substitutes," Biomaterials. Mar. 2008;29(9): 1147-1158.

Lynn et al., Degradable poly(β-amino esters): synthesis, characterization, and self-assembly with plasmid DNA, J. Am. Chem. Soc c., 2000; 122(44):10761-10768.

Matteini et al., "Microscopic characterization of collagen modifications induced by low-temperature diode-laser welding of corneal tissue," Lasers in surgery and medicine 2007;39(7):597-604.

Maury et al., "In-vitro development of corneal epithelial cells on a new hydrogel for epikeratoplasty," J Mater Sci Mater Med. Sep. 1997;8(9):571-576.

Mcdonald, "The future direction of refractive surgery," J Refract Surg 1988; 4(5):158-168.

Mclaughlin et al., "Regeneration of corneal cells and nerves in an implanted collagen corneal substitute," Cornea. Jun. 2008;27(5): 580-589.

Menabuoni et al., "Laser-assisted corneal welding in cataract surgery: Retrospective study," J Cataract Refract Surg. Sep. 2007;33(9):1608-1612.

Merrett et al., "Tissue-engineered recombinant human collagen-based corneal substitutes for implantation: performance of type I versus type III collagen," Invest Ophthalmol Vis Sci. Sep. 2008;49(9): 3887-3894.

Moore et al., "Fate of lyophilized xenogeneic corneal lenticules in intrastromal implantation and epikeratophakia," Invest Ophthalmol Vis Sci. Mar. 1987;28(3):555-559.

Nader, "Learning a new language: understanding the terminology of wavefront-guided ablation," OSN SuperSite. Downloaded from the Internet: <<http://www.osnsupersite.com/print.aspx?rid=6912>>.

Nakamura, "Histopathological and immunohistochemical studies of lenticules after epikeratoplasty for keratoconus," British Journal Ophthalmology 2005;89:841-846.

Ophthalmology Times, "New LASIK device: CIBA Vision to market subepithelial separator ", Aug. 1, 2002, 1 page only.

Pierce Crosslinking Reagents Technical HandBook, pp. 16-23. downloaded from the Internet:<<http://http://www.piercenet.com/files/1601361Crosslink.pdf.>>.

Rafat et al., "PEG-stabilized carbodiimide crosslinked collagen-chitosan hydrogels for corneal tissue engineering," Biomaterials. Oct. 2008;29(29): 3960-3972.

Rafat et al., "Surface modification of collagen-based artificial cornea for reduced endothelialization" J Biomed Mater Res A. Mar. 20, 2008. [Epub ahead of print].

Richards et al., "The relation of the corneal surface to the permanence of glued-on contact lenses," Can J Ophthalmol. Apr. 1971;6(2):98-103.

Ruben "Adhesive keratoprostheses," Trans Ophthalmol Soc U K. 1970;90:551-564.

Schmitz, 'Excimer laser "corneal shaping": a new technique for customized trephination in penetrating keratoplasty,' Graefe's Archive for Clinical and Experimental Ophthalmology, May 2003; 241:423-431.

Shimmura et al. "Biocompatibility of Collagen-based Blended Biomaterials" Invest Ophthalmol Vis Sci 2002;43: E-Abstract 2997. © 2002 ARVO.

Shimmura et al., "Collagen-poly(N-isopropylacrylamide)-based membranes for corneal stroma scaffolds.," Cornea. Oct. 2003;22(7 Suppl): S81-88.

Stenzel et al., "Collagen as a biomaterial," Annu. Rev. Biophys. Bioeng. 1974; 3:231-253.

Stile et al., "Poly(N-isopropylacrylamide)-Based Semi-interpenetrating Polymer Networks for Tissue Engineering Applications. 1. Effects of Linear Poly(acrylic acid) Chains oil Phase Behavior" Biomacromolecules, 2002; 3:591-600.

Stile et al., "Synthesis and Characterization of Injectable Poly(N-isopropylacrylamide)-Based Hydrogels That Support Tissue Formation in Vitro" Macromolecules, 1999; 32:7370-7399.

Stile et al., "Thermo-Responsive Peptide-Modified Hydrogels for Tissue Regeneration" Biomacromolecules 2001; 2(1): 185-194.

Suuronen et al., "Functional innervation in tissue engineered models for in vitro study and testing purposes," Toxicol Sci. Dec. 2004;82(2):525-533.

Suuronen et al., "Innervated human corneal equivalents as in vitro models for nerve-target cell interactions," The FASEB Journal. 2004;18:170-172.

Suuronen et al., "Tissue-engineered injectable collagen-based matrices for improved cell delivery and vascularization of ischemic tissue using CD133+ progenitors expanded from the peripheral blood," Circulation. Jul. 4, 2006;114(1 Suppl)I138-4.

Sweeney et al., "A synthetic polymer as a corneal onlay ," [ARVO Abstract] Invest Ophthalmol Vis Sci 40(4),S638Abstract nr 3361.

Trinkaus-Randall et al. "Biological response to a synthetic cornea" J. Controlled Release 1998; 53(1-3):205-214.

Trinkaus-Randall et al. "Implantation of a synthetic cornea: design, development and biological response," Artif Organs. Nov. 1997;21(11):1185-1191.

Tsai et al., "Reconstruction of damaged corneas by transplantation of autologous limbal epithelial cells", The New England Journal of Medicine Jul. 2000, 343(2):86-93.

Vascotto et al., "Localization of candidate stem and progenitor cell markers within the human cornea, limbus, and bulbar conjunctiva in vivo and in cell culture," Anat Rec A Discov Mol Cell Evol Biol. Aug. 2006;288(8):921-931.

Vernon et al., "Thermally reversible polymer gels for biohybrid artificial pancreas" Macromol. Symp.1996;109:155-167.

Vinciguerra et al., "Butterfly laser epithelial keratomileusis for myopia," Journal of refractive surgery 2002;18(3 Suppl):S371-3.

Yoshida et al., "Comb-type grafted hydrogels with rapid deswelling response to temperature changes" Nature, Mar. 16, 2002; 374:240-242.

U.S. Appl. No. 60/715,411, filed Sep. 9, 2005.

US 6,773,442, 08/2004, Pallikaris et al. (withdrawn)

* cited by examiner

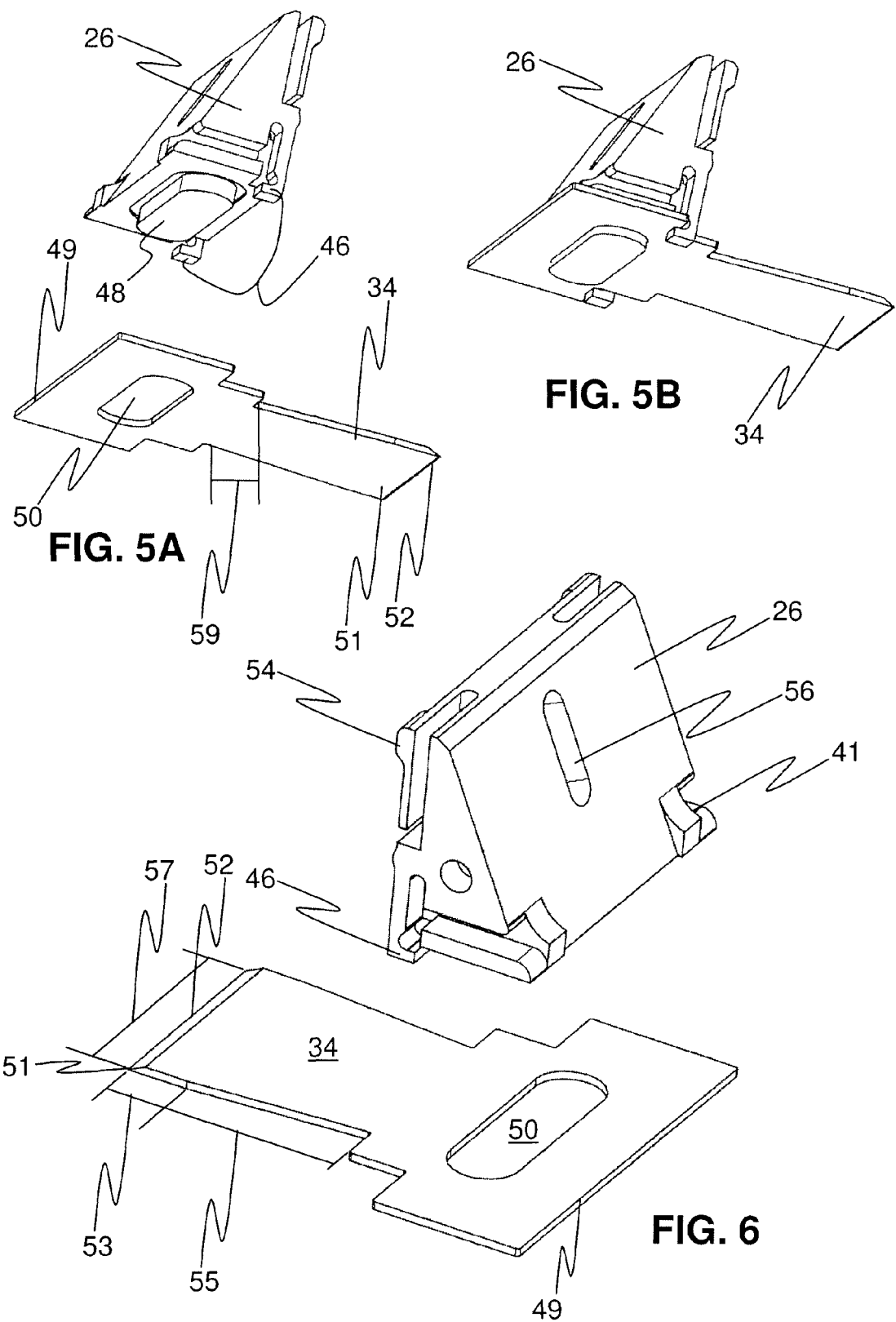

CORNEAL EPITHELIAL POCKET FORMATION SYSTEMS, COMPONENTS AND METHODS

CROSS-REFERENCE TO RELATED APPLICATIONS

This application claims the benefit of U.S. Provisional Application No. 60/790,874, filed Apr. 10, 2006, the contents of which are hereby expressly incorporated herein by reference.

FIELD OF THE INVENTION

The present invention is directed to systems, components, and methods for forming an epithelial pocket in a cornea of an eye of an individual.

BACKGROUND

Photo-refractive keratectomy (PRK), laser-assisted in situ keratomileusius (LASIK), and laser-assisted subepithelial keratomileusius (LASEK) are procedures performed on patients to improve a patient's vision by ablating intrastromal corneal tissue. PRK and LASIK procedures involve forming a flap of corneal tissue to expose the corneal stroma of an eye undergoing a surgical procedure. Typically, a corneal flap formed during a PRK or LASIK procedure has a thickness greater than 100 micrometers, for example, from about 130 micrometers to about 180 micrometers. Thus, a cut is made into the corneal stroma at a depth greater than 100 micrometers from the anterior or exterior surface of the eye. In comparison, the LASEK procedure involves forming a flap of corneal epithelium or a corneal epithelial flap. The LASEK procedure involves making a cut about 55 micrometers deep (e.g., a depth equal to or slightly greater than the thickness of a healthy adult corneal epithelium), and applying ethanol to loosen the corneal epithelial tissue and facilitate separation of the corneal epithelial flap from the underlying Bowman's membrane.

Examples of microkeratomes and related components useful for cutting corneal tissue in ablative procedures include those described in U.S. Pat. Nos. 5,496,339; 5,690,657; 6,071,293; and U.S. Patent Publication No. 20050251185.

Corneal onlays have been proposed as an alternative to these ablative procedures. A corneal onlay may be understood to be a corneal implant, and more specifically, an implantable ocular device or lens, that is placed on or anterior to Bowman's membrane, for example, between Bowman's membrane of the cornea of an eye and the corneal epithelium of the eye. Since corneal onlays are devices implanted into the eye of a patient, corneal onlays provide the opportunity to improve a patient's vision for long periods of time, but also provide a reversible procedure to correct refractive error. These procedures may result in improvements in a patient's vision without the need for spectacles or contact lenses.

Previously described approaches of using corneal onlays required complete removal or abrasion of the corneal epithelium to expose the underlying Bowman's membrane. It was postulated that placement of a corneal onlay on a deepithelialized Bowman's membrane would be helpful in improving a patient's vision. However, such procedures required corneal epithelial cells to grow and migrate over the corneal onlay, and the procedures presented significant issues of corneal epithelial undergrowth beneath the implanted corneal onlay. More recently, procedures for implanting corneal onlays have been proposed which include implanting a corneal onlay under a corneal epithelial flap or in a corneal epithelial pocket. For example, see U.S. Patent Publication Nos. 20030220653; 20050070942; 20050080484; 20050124982; and 20060052796; and International Patent Publication Nos. WO 2005/030102; WO 2005/049071; and WO 2006/007408.

While covering corneal onlays with corneal epithelial flaps provides some advantages, the corneal onlays may be prone to becoming decentered after the surgical procedure. Corneal epithelial pockets, that is pockets formed between the corneal epithelium and the corneal Bowman's membrane, can be effective in reducing decentration of the implanted corneal onlay after the surgical procedure, among other things.

A need remains for new systems and system components that are effective in forming a pocket between a corneal epithelium of an eye of a patient and the underlying Bowman's membrane. In other words, an existing problem relates to forming a corneal onlay implantation site which is associated with reduced decentration of an implanted corneal onlay compared to an implanted corneal onlay located beneath a corneal epithelial flap. In addition, a need remains for systems and system components which can separate substantially all of the corneal epithelium from the underlying Bowman's membrane to provide an implantation site that is free of epithelial cells. It can be understood that another existing problem relates to forming a corneal epithelial pocket to provide a Bowman's membrane without corneal epithelial cells that can negatively affect a corneal onlay placed in the pocket.

SUMMARY

The present corneal epithelial pocket formation systems, components, and methods are relatively easy to use and enable a user, such as a physician, to reliably create a corneal epithelial pocket, that is a pocket between the corneal epithelium and the underlying Bowman's membrane, in an eye of a human patient with little difficulty and little discomfort to the patient. Corneal epithelial pockets formed using the present systems, components, and methods can be formed by or be understood to include a viable corneal epithelium and a Bowman's membrane that is separate from the separated corneal epithelium, and that is substantially free of corneal epithelial cells, for example, that is free of corneal epithelial cells that can negatively impact a corneal onlay or other vision enhancing device placed in the corneal epithelial pocket.

A corneal epithelial pocket formed with the present systems, components, and methods is dimensioned to accommodate a corneal onlay that provides a desired vision improvement or vision correction to the patient, or other suitable ophthalmic device. The present systems and components are configured to form a corneal epithelial pocket, which receives a corneal onlay and is associated with little, if any, movement of the onlay relative to the optic axis or pupil of the eye. For example, a corneal onlay will remain substantially centered relative to the optical axis of the eye when placed in a corneal epithelial pocket produced with the present systems and methods. The incision and pocket formed with the present systems and methods can heal quickly and are not typically associated with significant discomfort to the patient. After placement of a corneal onlay in a corneal epithelial pocket formed with the present systems, components, and methods, a patient's vision can be enhanced or improved for prolonged periods of time, such as months or years, without requiring the use of additional spectacles or contact lenses. The present systems, components, and methods separate a portion of the corneal epithelium from Bowman's membrane, which remains viable during the surgical procedure, during recovery from the surgical procedure, and after the healing period from the surgical procedure. The present systems, components, and methods can separate a portion of the corneal epithelium from Bowman's membrane substantially without leaving residual corneal epithelial cells in contact with Bowman's membrane. With the present systems and methods, the corneal epithelium is separated from Bowman's membrane so that no detectable epithelial cell undergrowth occurs when the corneal onlay is placed in the eye.

Unlike microkeratomes that cut lamellar flaps into the stroma of an eye, the present systems can separate a thinner layer of corneal tissue (i.e., the corneal epithelium) from the underlying Bowman's membrane. In addition, compared to microkeratomes that cut the corneal epithelium to form corneal epithelial flaps, the present systems can separate the corneal epithelium from the underlying Bowman's membrane without forming a corneal epithelial flap and without lifting the corneal epithelium to a degree that negatively affects the viability of the separated corneal epithelium. For example, unlike existing corneal epithelial flap forming systems, the present corneal epithelial pocket formation systems are structured or configured to separate the corneal epithelium from the underlying Bowman's membrane without stretching or otherwise damaging the corneal epithelium during formation of a corneal epithelial pocket. Thus, the separated layer of corneal epithelium that defines a portion of the corneal epithelial pocket is viable, and healing of the eye after a surgery can be facilitated.

Compared to other previously proposed corneal epithelial pocket formation systems, the present systems cleanly separate the corneal epithelium from the underlying Bowman's membrane to reduce the possibility that corneal epithelial cells will remain on Bowman's membrane and may lead to undesirable epithelial cell growth under a corneal onlay or other vision enhancing ophthalmic device placed in the pocket. The present systems, components, and methods are able to provide corneal epithelial pockets suitable for long term accommodation of corneal onlays or other vision enhancing ophthalmic devices due to unique blade configurations and interactions with a blade drive assembly that are not present in existing or previously described corneal epithelial flap or pocket formation systems.

The present systems and components can be structured or configured to form a separated portion of the corneal epithelium that remains attached to non-separated corneal epithelium along a major portion, such as at least about 50% or more than about 50%, of the perimeter of the separated portion of corneal epithelium. The epithelial pocket created with the present systems may be understood to be a cavity or receptacle located between a separated portion of corneal epithelium and the underlying Bowman's membrane. Unlike corneal epithelial flaps which can be folded over a hinge region of corneal epithelium to expose Bowman's membrane, corneal epithelial pockets formed with the present systems, components, and methods can be defined, at least in part, by a separated portion of corneal epithelium that cannot be substantially folded over to expose the underlying Bowman's membrane, for example, without damaging or destroying the separated portion of corneal epithelium.

The present systems comprise a corneal epithelium separator and a drive assembly. The drive assembly causes the corneal epithelium separator to separate a portion of the corneal epithelium from the underlying Bowman's membrane to form a corneal epithelial pocket, as described herein. As used herein, the corneal epithelium separator may also be referred to as a blade.

It has been discovered that in order to obtain a clean separation of the corneal epithelium and the Bowman's membrane and to form a pocket that comprises a viable corneal epithelium, a variety of factors are important in configuring corneal epithelial pocket formation systems. For example, blade orientation can be important. As discussed herein, the blade is oriented, relative to a head of the system or relative to a surface of the eye to be cut, to separate or cut the corneal epithelium from Bowman's membrane without stretching the corneal epithelium to a degree that would adversely affect the viability of the separated corneal epithelium. In addition, blade shape can be important. The present blades are shaped to separate the corneal epithelium from Bowman's membrane without damaging the sides of the pocket formed by the blade. The cutting edge of the blade can be important. For example, it has been found that a tip radius in a range of about 300 nm to about 800 nm is important for obtaining a clean separation of the corneal epithelium from Bowman's membrane. Compared to existing corneal flap formation systems, the blades of the present corneal epithelial pocket formation systems have maximum widths that are less than the maximum widths of the flap forming blades, and the blades of the present systems have lengths that are greater than flap forming blades. The relationship between an applanated area of the eye and the length of the blade cutting edge can also be important. Compared to corneal flap forming systems, the present systems provide an applanation area that has a transverse dimension that is greater than the distance in which the cutting edge of the blade moves. In addition, compared to other systems, controlling the vertical movement of the blade can be important to prevent undesired injury to the Bowman's membrane and reduce friction between the moving blade and other components of the system.

Embodiments of the present systems, components, and methods will be apparent from the following description and claims.

For example, a corneal epithelial pocket formation system comprises a corneal epithelial separator and a drive assembly. The system may comprise a cutting head and the separator or blade is a component of the cutting head. The cutting head can be attached to, coupled to, or otherwise extend from a housing which includes the drive assembly. It can be understood that the cutting head comprises or includes the blade or separator. The cutting head may also comprise an applanator that is structured to act on a portion of a patient's eye to facilitate separation of the corneal epithelium from Bowman's membrane with the blade. The cutting head can include or can be engaged with a suction ring to fix the system and the eye to be cut.

In certain embodiments, the blade or separator is oriented at an angle of about 0° or a 0° angle from a horizontal line relative to the applanated surface of an eye being cut. In certain embodiments, the blade has a distal cutting end that has a maximum width that is greater than a more proximal non-cutting end of the blade. In certain embodiments, the blade has a cutting edge at its distal end that has a tip radius in a range of about 300 nm to about 800 nm. In certain embodiments, the present blades have a maximum width that is less than the maximum width of the corneal epithelial pocket created with the blade. For example, a blade that creates an 8 mm wide pocket can have a maximum width in a range of about 6.5 mm to about 7.5 mm. The present blades can also have a blade length or maximum length that is greater than blade lengths for corneal epithelial flap blades. For example, the present blades may have a maximum length greater than 8 mm. Embodiments of the present blades may have a maximum length of about 14-15 mm. Embodiments of the present systems that include an applanator can also include a blade that has a cutting edge positioned at a distance from the applanator to control the presentation of the corneal epithelium relative to the blade and to control the separation force required to separate the corneal epithelium as a portion of an epithelial pocket without stretching or negatively affecting the viability of the separated corneal epithelium. For example, the distance between the blade cutting edge and the applanator can be greater than 160 micrometers, and in certain embodiments, the distance between the blade cutting edge and the applanator is at least 190 micrometers. Certain embodiments of the present systems comprise a cutting head, which comprises a blade, and a suction ring structured for placement on an eye to be cut. The cutting head can move relative to the suction ring along one or more guidance mechanisms. The guidance mechanisms can be located above the cutting edge of the blade in certain embodiments. Embodiments of systems that include an applanator provide an applanation area on the eye to be cut. The applanation area has a minimum transverse dimension, such as a width, that is greater than the maximum dimension of transversely moving or oscillating blade. As used herein, transverse movement of the blade refers to lateral or crosswise movement of the blade relative to the longitudinal movement of the blade or to the length of the blade. Thus, the cutting edge of the blade does not cut all the way to the edge of the applanated area. This configuration prevents the formation of a corneal epithelial flap and facilitates formation of a corneal epithelial pocket. In certain embodiments, the distance between the suction ring and the applanator is controlled to prevent or reduce damage to or cutting of the distal end of the epithelial pocket by the blade cutting edge. In certain embodiments, the systems comprise a blade holder that is removable from the cutting head. The blade holder is attached to the blade and facilitates guidance of the blade relative to the cutting head. The blade holder can include one or more springs or other biasing members, which may be additional physical components or functional properties of the blade holder, as discussed herein.

In at least one embodiment, including the illustrated embodiment described herein, a corneal epithelial pocket formation system comprises a cutting head that is attached to or extending from a housing member. The cutting head comprises a blade holder and a blade attached thereto. The blade is oriented in the cutting head at a 0° angle from a horizontal line. The blade has a cutting edge at its distal end with a tip radius in a range of about 300 nm to about 800 nm. The blade cutting edge has a width of 6.5 mm to 7.5 mm to create a pocket that has a maximum width of about 8 mm. The blade length is 14.5 mm. The distal end of the blade has a width that is greater than a more proximal region of the blade. For example, a 1-2 mm long blade portion extending from the distal end has a constant width of about 7 mm and the width of the blade narrows or decreases proximally from that 1-2 mm portion. The cutting head includes an applanator and the distance between the blade cutting edge and the applanator is at least 190 micrometers. The applanator provides an applanation area when placed on an eye that has a minimum width that is greater than the maximum width of the moving blade (e.g., greater than 8 mm for this embodiment). The blade is attached to a spring loaded blade holder that is attached to the cutting head. The blade holder is actuated by a motor assembly and the blade holder provides or controls the guidance of the blade relative to the cutting head. The cutting head is attached to a suction ring that is structured for placement on an eye of a patient, and the guidance between the cutting head and the suction ring is located above the blade cutting edge.

Other embodiments of the present invention relate to system components of the systems described herein. For example, an embodiment of the present invention includes the combination of the blade holder and the corneal epithelial pocket forming blade. The combination can be understood to be a corneal epithelial pocket cutting assembly. The assembly can be separately packaged and provided in sterile conditions to be attached to a cutting head of the present systems. After use, the cutting assembly can be disposed or sterilized and reused if desired. In certain embodiments, disposable cutting assemblies are desirable to minimize potential for contamination and to reduce the additional work required to sterilize medical instruments. Further embodiments relate to the corneal epithelial pocket forming blades which can be provided separately from the blade holder or the systems in general.

Embodiments of the present invention also related to methods of using the present systems and system components. For example, embodiments include methods of enhancing vision of a patient using the systems and/or system components described herein. Embodiments also include the use of the present blades, cutting assemblies, and other components in the manufacture of a medical or surgical device for enhancing vision of a patient.

As can be appreciated from the foregoing and following description, each and every feature described herein, and each and every combination of two or more of such features, is included within the scope of the present invention provided that the features included in such a combination are not mutually inconsistent. In addition, any feature or combination of features may be specifically excluded from any embodiment of the present invention.

Additional aspects and advantages of the present invention are set forth in the following description and claims, particularly when considered in conjunction with the accompanying drawings.

BRIEF DESCRIPTION OF THE DRAWINGS

FIG. 5A is an exploded view of a blade holder and blade configured for use with the present corneal epithelial pocket formation systems.

FIG. 5B is a perspective view of the blade holder and blade of FIG. 5A when assembled.

FIG. 6 is an exploded rear perspective view of the blade holder and blade of FIG. 5A.

DETAILED DESCRIPTION

Figure 1:
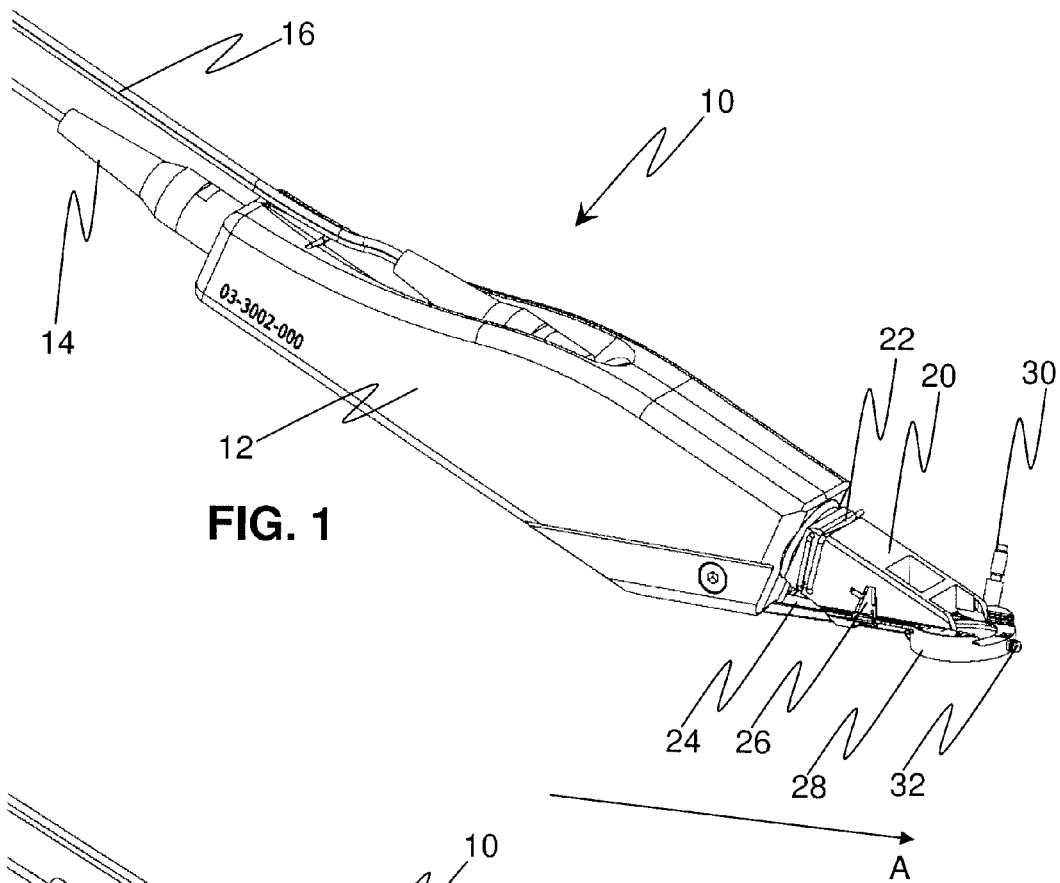
FIG. 1 is a perspective view of a corneal epithelial pocket formation system.

The present corneal epithelial pocket formation systems, components, and methods are effective in forming a corneal epithelial pocket in an eye of a patient, such as a human patient. The epithelial pockets are dimensioned to accommodate a corneal implant that is placed in the pocket to enhance, improve, or correct a patient's vision. Corneal implants which can be placed in the epithelial pockets include ophthalmic devices with or without refractive powers. Thus, corneal implants can refer to devices such as lenses, filters, blanks, and the like. In certain embodiments, the corneal implants are lenses and are referred to herein as corneal onlays. The present systems, components, and methods result in a portion of corneal epithelium that has been separated from the underlying Bowman's membrane. The separated portion of corneal epithelium remains viable during and after the surgical procedure.

The human cornea consists of five layers, namely, the corneal epithelium, the Bowman's membrane, the stroma, Descemet's membrane, and the endothelium. The corneal epithelium usually is about 5-6 cell layers thick (approximately 50-55 micrometers thick), and generally regenerates when the cornea is injured. The corneal epithelium lines the anterior or exterior surface of cornea, provides a relatively smooth refractive surface, and helps prevent infection of the eye. The corneal stroma is a laminated structure of collagen which contains cells, such as fibroblasts and keratocytes, dispersed therein. The stroma constitutes about 90% of the corneal thickness. The anterior portion of the stroma, which underlies the epithelium, is a cellular and is known as Bowman's membrane. Bowman's membrane is located between the epithelium and the stroma and is believed to protect the cornea from injury. The corneal endothelium typically is a monolayer of low cuboidal or squamous cells that dehydrates the cornea by removing water from the cornea. An adult human cornea is typically about 500 µm (0.5 mm) thick and is typically devoid of blood vessels.

The present systems, components, and methods form corneal epithelial pockets that are dimensioned to accommodate a corneal implant. As used herein, and as described above, a corneal epithelial pocket can be understood to be a cavity, void, or corneal implant receptacle defined between a separated portion of corneal epithelium and the underlying Bowman's membrane. Thus, a corneal epithelial pocket can be defined by a separated portion of corneal epithelium and the underlying Bowman's membrane. Unlike corneal epithelial flaps, the present corneal epithelial pockets include a separated portion of corneal epithelium that remains attached to the Bowman's membrane along a major portion of the perimeter of the separated portion. For example, at least 50%, at least 60%, at least 70%, at least 80%, or at least 90% of the perimeter of the separated portion remains attached to Bowman's membrane. Thus, a small incision can be made in the epithelium through which a corneal epithelial separator can be inserted to form a cavity that is substantially perimetrically surrounded by corneal epithelium that is attached to Bowman's membrane.

Importantly, corneal epithelial pockets can be formed without exposing the eye to ethanol and without forming an epithelial flap. The separated portion of corneal epithelium remains viable, and is cleanly separated from the underlying Bowman's membrane so that epithelial cells do not grow, migrate, or divide between the corneal implant placed in the pocket and the underlying Bowman's membrane.

Reference will now be made in detail to the present embodiments of the invention, some examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, front, backward, forward, horizontal, vertical, distal, proximal, anterior, posterior, superior, inferior, temporal, and nasal are used with respect to the accompanying drawings. Such directional terms should not be construed to limit the scope of the invention in any manner.

Although the disclosure herein refers to certain embodiments, it is to be understood that these embodiments are presented by way of example and not by way of limitation. The intent of the following detailed description, although discussing exemplary embodiments, is to be construed to cover all modifications, alternatives, and equivalents of the embodiments.

Figure 2:
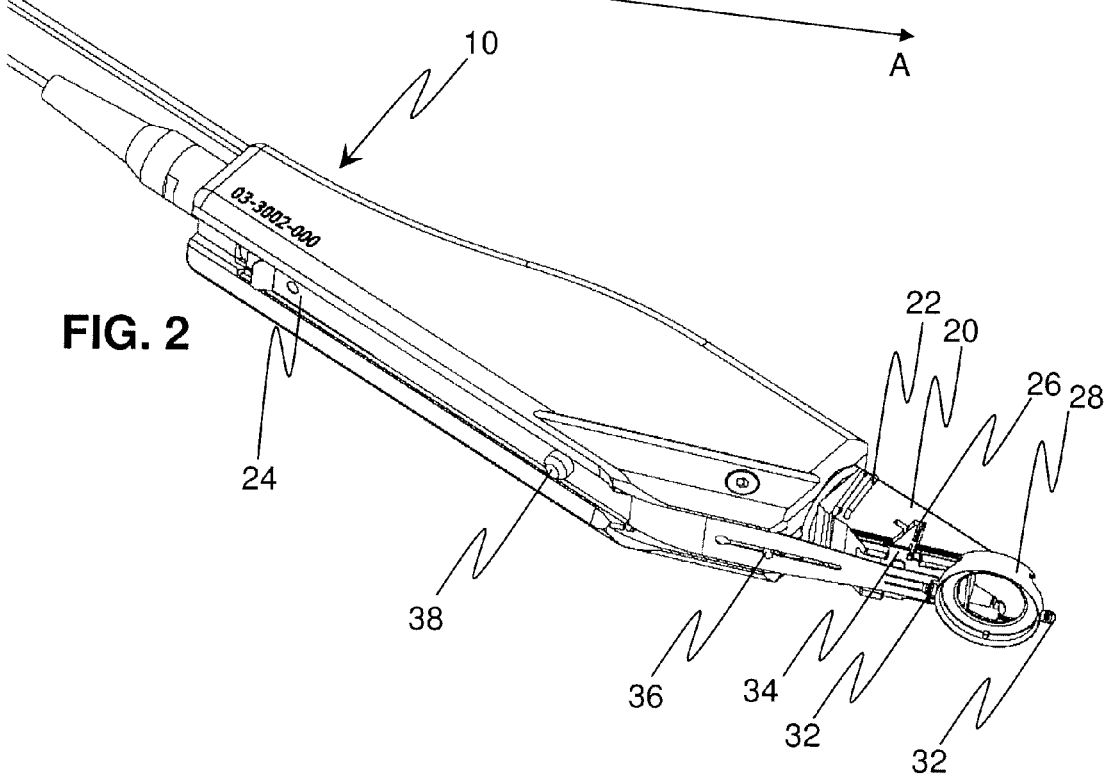
FIG. 2 is a perspective view of the system of FIG. 1 when viewed from below the system.

In reference to FIG. 1 and FIG. 2, a corneal epithelial pocket formation system 10 includes a cutting head 20 and a blade 34 coupled to the cutting head 20. The blade 34 can be directly or indirectly attached to the cutting head 20. For example, one or more intermediate members or devices, such as the blade holder 26, can be used to attach a portion of the blade 34 to a portion of the cutting head 20.

The blade 34 is oriented when coupled to the cutting head 20 so that a viable separated portion of corneal epithelium is maintained during formation of a corneal epithelial pocket. This viable separated portion of corneal epithelium can be understood to be a pocket-defining portion of corneal epithelium. For example, the present blades 34 are oriented so that during formation of a corneal epithelial pocket, the corneal epithelium is not substantially lifted, stretched, or otherwise injured in a manner that would negatively affect the viability of the corneal epithelium. Maintaining a viable corneal epithelium is important to improve the likelihood of a successful vision correcting or vision enhancing procedure. Unlike systems that form corneal epithelial flaps, the present systems are able to separate a portion or layer of corneal epithelium that remains attached to non-separated portions of corneal epithelium without stretching the corneal epithelium. In certain embodiments, including the illustrated embodiment, the blade 34 is oriented at an angle of about 0° or at about a 0° angle relative to the longitudinal movement path of the blade during the formation of the corneal epithelial pocket. An example of the longitudinal movement path is shown by arrow A in FIG. 1. In comparison, some epithelial flap forming systems orient the epithelial separating blade at an angle of about 25° from the longitudinal movement path of the blade. In a particular embodiment, the blade 34 is oriented exactly at a 0° angle. However, in additional embodiments, some variation in orientation angle can be accommodated. Thus, it can be understood that certain embodiments of the present systems have a blade that is oriented at about a 0° angle from a straight line extending along or parallel to a longitudinal guidance path of the blade, such as the path represented by arrow A.

The system 10 illustrated in FIG. 1 and FIG. 2 also includes a housing 12. The housing 12 comprises one or more motors (not shown). The motor or motors provide movement of the blade 34 of the cutting head 20. For example, one of the motors can control longitudinal movement of the blade 34 relative to the cutting head 20, and another motor can provide transverse movement of the blade 34 relative to the longitudinal movement. For example, the blade 34 may oscillate or vibrate from side to side as the blade 34 moves forward and/or backwards. A motor for longitudinal movement of the blade may be understood to be an advance motor, and a motor for the transverse movement of the blade may be understood to be an oscillation motor. The motor or motors can be actuated or controlled by one or cables. For example, the illustrated system can comprise an advance motor cable 14, and an oscillation motor cable 16.

The housing 12 and components thereof can be similar to microkeratome housings described in U.S. Pat. No. 6,071, 293 or U.S. Pat. Pub. No. 2005/0251185. In addition, the housing 12 may be similarly or identically structured to an epithelial flap forming microkeratome system available from Gebauer GmbH (Germany) under the tradename, EPIVISION™.

As shown in FIG. 1 and FIG. 2, the cutting head 20 is attached or coupled to the housing 12 using a locking device 22. The blade 34 is indirectly attached to the advance motor via physical blade connector element 24, which is illustrated as a metal band. The blade 34 is also directly attached to the blade holder 26 which receives input from the oscillation motor to cause the blade 34 to oscillate or vibrate. As shown in FIG. 2, the physical blade connector element 24 may include a pushing aid 38 and a threading aid 36. Although the blade connector element 24 is illustrated as a metal band, other blade connector elements can be formed from other structurally different items, including rods, cables, and the like.

Figure 3:
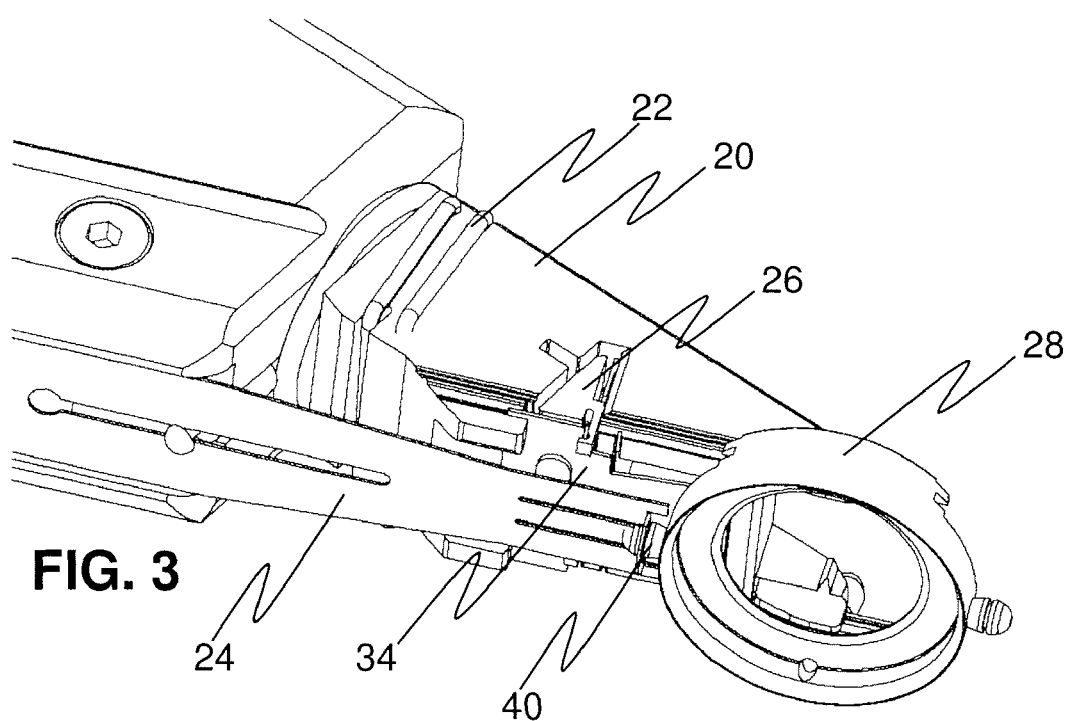
FIG. 3 is a magnified view of the cutting head portion of the system of FIG. 1.

The cutting head 20 is engageable with a suction ring 28. The suction ring 28 includes a vacuum connector 30 and one or more driving pins 32. FIG. 3 illustrates a magnified view of a bottom portion of the cutting head 20. As can be seen in FIG. 3, the proximal driving pin 32 also includes a shackle 40 which fastens the metal band 24 to the suction ring 28. Although the illustrated suction ring 28 is a separate component from the cutting head 20 and can be removed and handled independently of the cutting head, other embodiments of the present systems can include a cutting head that includes an integral suction ring or other ocular fixation device.

Figure 4:
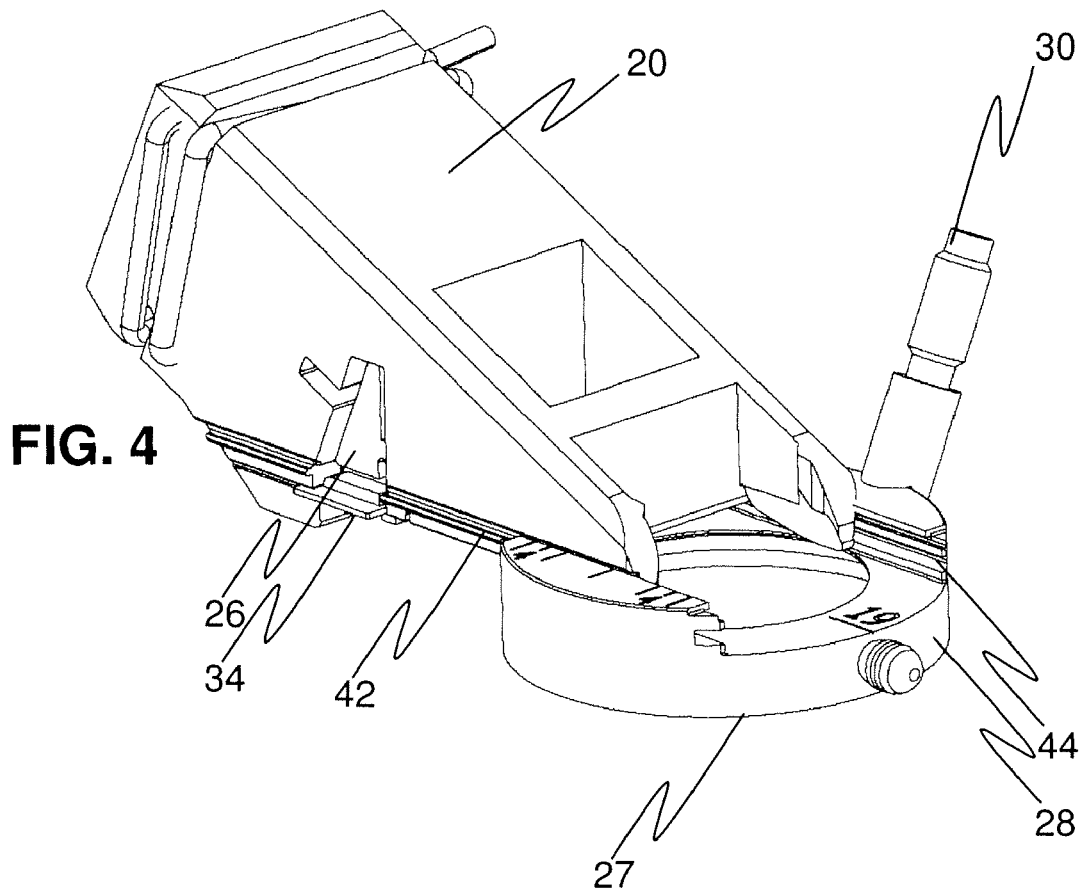
FIG. 4 is a magnified view of the cutting head portion of the system of FIG. 1 when viewed from above the system.

As shown in FIG. 4, the suction ring 28 includes a cornea contacting portion 27 and an opposing cutting head guidance portion 44. The cutting head 20 also includes a guidance portion 42. The two guidance portions 42 and 44 engage with each other to provide slidable movement of the cutting head 20 and suction ring 28. The guidance portions 42 and 44 may also be understood to be cutting head and suction ring guiding surfaces.

FIG. 5A and FIG. 6 provide exploded views of a cutting assembly of the present systems, and FIG. 5B provides an assembled view of the cutting assembly. The cutting assembly includes the blade 34 and the blade holder 26. The present blades 34 comprise a cutting edge surface 52 at the distal end 51 of the blade 34. The cutting edge surface 52 is effective in separating the corneal epithelium from the underlying Bowman's membrane of the eye without leaving residual corneal epithelial cells in contact with Bowman's membrane that may result in corneal epithelial cell growth between a corneal implant located in the corneal epithelial pocket and the underlying Bowman's membrane. In certain embodiments, it is preferable that no corneal epithelial cells remain adjacent Bowman's membrane. However, in other embodiments, if any epithelial cells are present, they are not sufficient to cause epithelial cell undergrowth of the corneal implant. The cutting edge surface 52 of the present blades 34 can be effective in separating the corneal epithelium from the underlying Bowman's membrane without leaving any visually identifiable corneal epithelial cells adjacent to the underlying Bowman's membrane. Thus, for example, when corneal tissue is histologically examined, microscopic examination can reveal that the Bowman's membrane is completely free of any visually identifiable corneal epithelial cells. Such a clean separation can also be verified by using one or more in vivo markers, including fluorescent markers, that selectively stain corneal epithelial cells. Typically, visual identification of epithelial cells is accomplished using a magnifying instrument, including microscopes. The epithelial cells can be visualized under various magnifications as understood by persons of ordinary skill in the art. For example, the epithelial cells, or a lack thereof, can be verified by examining the separated portion at a magnification of 10×, 20×, 25×, 50×, or even 100×. However, when certain markers are used to stain epithelial cells, such as fluorescent markers, it may be possible to determine the presence or absence of epithelial cells on Bowman's membrane without a magnifying instrument. In the illustrated embodiment, the cutting edge surface 52 has a cross-sectional radius less than 1 micrometer. For example, the cutting edge surface 52 can have a cross-sectional radius from about 300 nanometers to about 800 nanometers.

While the present corneal epithelial pocket forming blades 34 may have a variety of shapes and dimensions, certain embodiments have a maximum width 57 equal to the length of the cutting edge surface 52 of the blade 34. Furthermore, embodiments of the present blades 34 can have a maximum width 57 at the distal end 51 of the blade 34, and a second width 59 at a more proximal location that is less than the maximum width 57. Still further, the blade 34 may have a distal portion 53 that has a width 57 effective in forming a corneal epithelial pocket that includes first and second lateral epithelial pocket edges attached to Bowman's membrane during transverse oscillation of the blade, and an adjacent proximal portion 55 that has a width 59 effective in preventing contact of the proximal portion 55 with the first or second lateral pocket edges during oscillation of the blade.

The blade 34 also has a proximal end 49 and includes an aperture 50 structured to contact a protrusion member 48 of the blade holder 26. The protrusion member 48 can act as a centering mechanism for the blade 34, and is represented by a portion of the blade holder 26 that extends downwardly to engage with aperture 50 of the blade 34. The blade holder 26 can also include one or more vertical securement devices, which in the illustrated embodiment are shown as a plurality of hooks 46.

As shown in FIG. 6, the blade holder 26 includes a first guiding area 41 and a second guiding area 54. In addition, the blade holder 26 also includes an oscillation slot or aperture 56 to accommodate an actuator that causes oscillation of the blade 34. For example, when the blade holder 26 is engaged with the cutting head 20, as shown in FIG. 1 for example, an oscillation motor in the housing 12 can engage with the blade holder 26 to cause transverse oscillation of the blade 34.

As evident from the figures, the blade holder 26 can be understood to be a removable blade holder that can be inserted into and removed from the cutting head 20. The blade holder 26 of the illustrated embodiment is a spring loaded blade holder. For example, using one or more biasing forces, the blade holder 26 can provide a desired guidance of the blade 34 during a surgical procedure. Unlike corneal epithelial flap producing systems in which the entire blade is guided by the cutting head, the present systems primarily guide the blade 34 using the spring loaded removable blade holder 26, and only guide the proximal end of the blade 34 with the cutting head. In the illustrated embodiment, the blade holder 26 is formed from a resilient material, such as plastic materials, that have an inherent resiliency incorporated into the formed blade holder. The particular configuration of the blade holder 26 and the spring forces provided by the blade holder can be empirically determined using routine methods known to persons of ordinary skill in the art. For example, the blade holder 26 is structured or configured to reduce vertical movement of the blade 34, including the cutting edge surface 52, during a cutting procedure. Vertical movement of the blade can be especially significant and cause injury to the eye due to the length of the blade, especially when compared to blade lengths of epithelial flap forming blades and related microkeratomes. In addition, the resiliency of the blade holder can be selected to minimize the friction between one or more portions of the blade holder and one or more portions of the cutting head that may result in damage to the cutting head.

Figure 7A:
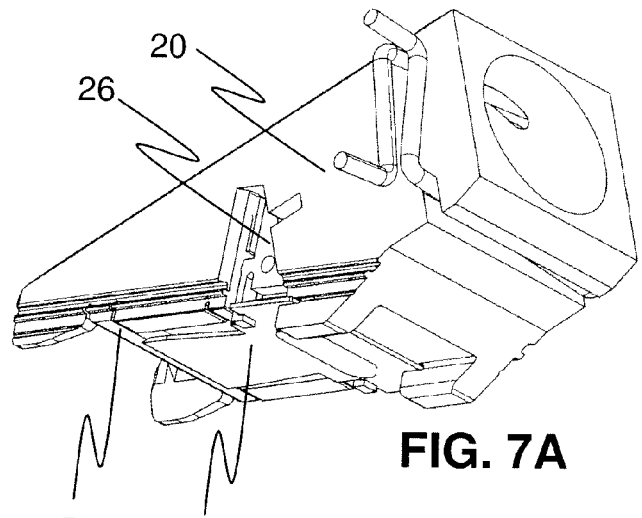
FIG. 7A is a perspective view of a blade holder and blade when assembled with a cutting head of the present systems.
Figure 7B:
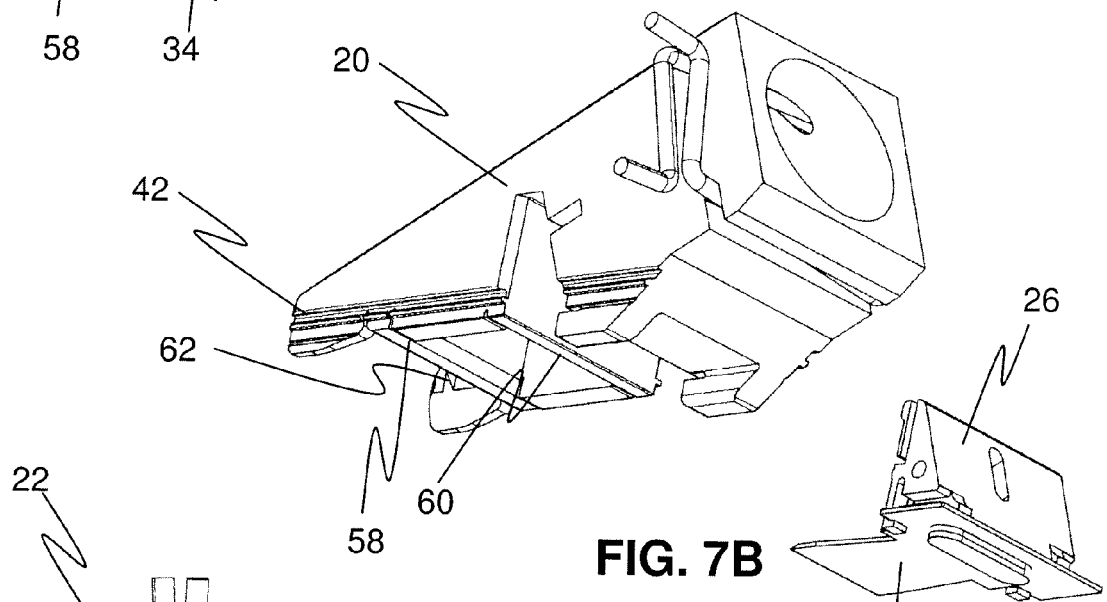
FIG. 7B is an exploded perspective view of the blade holder and blade and cutting head of FIG. 7A.
Figure 8:
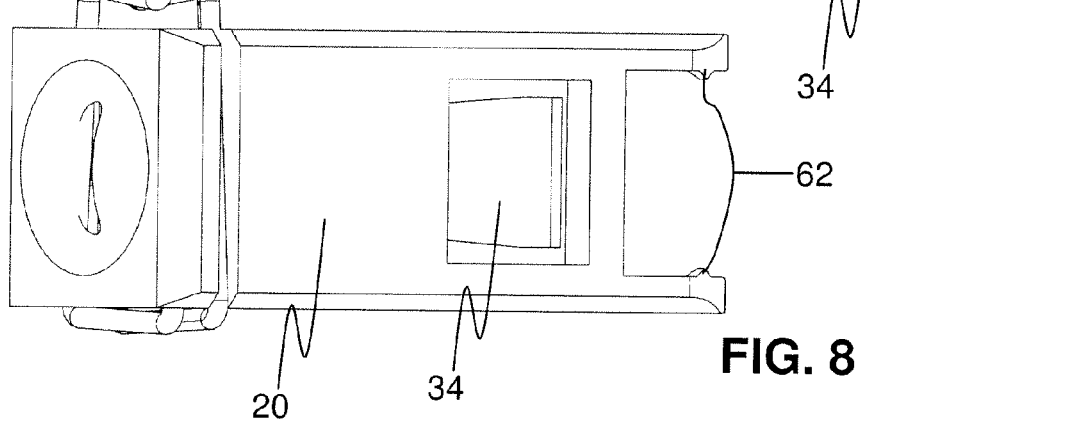
FIG. 8 is a magnified view of the cutting head of the present systems when viewed from below the cutting head.

An exploded view of the cutting assembly and the cutting head 20 are shown in FIG. 7B, and an assembled view of the cutting assembly and cutting head 20 are shown in FIG. 7A. The illustrated cutting head 20 includes an applanator 58, a support bar 60, and a plurality of markings 62. The markings 62 are shown in FIG. 8 as being located on either side of the cutting head 20 and extending towards the cutting region of an eye.

The applanator 58 provides an applanation area on an eye on which the surgical procedure is being performed. In the illustrated embodiment, the applanation area has a minimum width that is greater than the maximum transverse dimension of the distal end 51 of the blade 34 during oscillation of the blade. For example, the width of the applanation area is greater than the maximum width spanned by the oscillating blade. By providing a wider applanation area, it is possible to cut a portion of the corneal epithelium without contacting the sides of the applanated area and thereby reduce or prevent cutting of the sides of the cut portion. By maintaining the integrity of the sides of the separated corneal epithelium, corneal epithelial pockets can be effectively produced. In comparison, epithelial flap forming systems cut a portion of the corneal epithelium that is greater than the applanation area thereby only providing an attached region at the distal end of the cutting path.

The distance between the cutting edge surface 52 and the applanator 58 can be important for controlling the angle in which the corneal tissue is presented to the cutting edge surface 52, and determining how large the separation force required to separate the epithelium from Bowman's membrane. In certain embodiments, the distance between the applanator and the cutting edge surface is greater than 160 micrometers. In additional embodiments, the distance is at least 190 micrometers or more.

When the blade holder 26 is engaged with the cutting head 20, the blade cutting edge surface 52 is located between the cornea contacting portion 27 of the suction ring 28 and the cutting head guiding portion 44 of the suction ring during formation of the corneal epithelial pocket.

In view of the disclosure herein, it can be appreciated that the present systems and components can include one or more elements or features to provide corneal epithelial pockets in an eye of a human patient. For example, one embodiment of the present systems can include a suction ring 28, a cutting head 20, and a housing 12. The suction ring 28 includes a cornea contacting portion 27 and an opposing cutting head guidance portion 44. The cutting head 20 is in contact with the cutting head guidance portion 44 of the suction ring 28. The cutting head 20 includes an applanator 58 that is structured, such as sized and shaped, to provide an applanation area on the cornea of an eye during a corneal epithelial pocket forming procedure. The cutting head 20 also includes a spring loaded blade holder 26, and a blade 34 extending from the spring loaded blade holder 26 at about a 0° angle from a straight line extending along a longitudinal guidance path (arrow A in FIG. 1) of the blade 34. The blade 34 has a distal end portion 53 that includes a cutting edge surface 52 that defines a maximum width 57 of the blade 34. The blade 34 also has a proximal end portion 55 that has a width 59 that is less than the width 57 of the distal end portion 53. The housing 12 includes a motor that provides movement of the blade 34. The movement includes transverse oscillating movement of the blade 34, which causes the cutting edge surface 52 to oscillate and form an epithelial pocket having a maximum transverse dimension that is less than a minimum transverse dimension of the applanation area provided by the applanator 58.

The present components can be used to produce a corneal epithelial pocket formation system, as described herein. The use or method of producing a corneal epithelial pocket formation system includes providing a corneal epithelial pocket forming blade, such as the blades disclosed herein, retained by a spring loaded blade holder, and engaging the blade holder with a cutting head of a motorized device. For example, the illustrated cutting assembly can be attached to the cutting head 20 described herein. The blade of the engaged blade holder is oriented to maintain a viable separated pocket defining portion of corneal epithelium of an eye of a patient during formation of the corneal epithelial pocket of the eye.

The components of the present systems can be produced from conventional materials used in production of medical and surgical instruments. For example, materials from which the present components can be produced include plastic materials and metal materials. For example, the blade holder 26 can be formed of plastic. The blade 34 can be formed from stainless steel or other suitable materials. The blade can be coated or otherwise modified to provide a smooth surface with a small coefficient of friction to reduce damage to the corneal epithelium. The components can be machined or formed using any conventional method known to persons of ordinary skill in the art.

The present systems can be used in methods of enhancing vision of a patient by forming a corneal epithelial pocket in an eye of a patient. For example, one method may include administering an anesthetic to the patient, such as by topically administering an anesthetic composition to the eye of the patient, and placing the suction ring 28 on the eye of the patient and applying a vacuum to the suction ring. The cutting head 20 can be engaged with the suction ring 28. The blade 34 can be actuated to move forward and oscillate from left to right to cut the corneal epithelium. The separated portion of corneal epithelium passes over the top of the blade 34 without substantially stretching or damaging the epithelial cells. When an epithelial pocket of a desired length has been produced, the oscillation of the blade can be stopped and the blade can be withdrawn. Subsequently, a corneal implant can be placed in the corneal epithelial pocket. The methods may also include administering cool saline compositions to the eye, such as by applying saline eye drops which are provided at a temperature less than 20° C., for example, between about 4° C. and about 15° C., to the eye.

The present invention also relates to components of the present systems. For example, an embodiment of the present invention includes a package which includes a corneal epithelial pocket forming blade, such as the blades disclosed herein, and a spring loaded blade holder, such as the blade holders disclosed herein. The spring loaded blade holder is removably engageable with a cutting head of a motorized device, as described herein. The blade holder is structured to retain the blade at an orientation effective in maintaining a viable separated pocket defining portion of corneal epithelium of an eye of a patient during formation of the corneal epithelial pocket of the eye when the blade holder is engaged with the cutting head. In certain embodiments, the blade and blade holder of the present packages are sterilized. Thus, examples of the blade and blade holders can be ready for single use and disposed of after formation of a corneal epithelial pocket.

Another embodiment of the present invention relates to blades for corneal epithelial pocket formation systems. The present blades 34 comprise a distal end portion 53 and an adjacent proximal portion 55, as shown in FIG. 6. The blades 34 also comprise a cutting edge surface 52 located at the distal end 51 of the blade. The cutting edge surface 52 is effective in separating a portion of corneal epithelium of an eye of a patient from the underlying Bowman's membrane of the eye during formation of a corneal epithelial pocket without leaving residual corneal epithelial cells in contact with Bowman's membrane that may result in corneal epithelial cell growth between a corneal implant located in the corneal epithelial pocket and the underlying Bowman's membrane. The adjacent proximal portion 55 is structured to be located in the corneal epithelial pocket during formation of the pocket and the proximal portion 55 has a width less than the width of the distal end portion 53.

While this invention has been described with respect to various specific examples and embodiments, it is to be understood that the invention is not limited thereto and that it can be variously practiced within the scope of the following claims.

A number of publications and patents have been cited hereinabove. Each of the cited publications and patents is hereby incorporated by reference in its entirety.

What is claimed is:

1. A system for forming a pocket in a cornea of an eye, the cornea having a Bowman's membrane and an epithelium disposed over the Bowman's membrane the epithelium having a thickness, the system comprising:
    a cutting head;
    an applanator having a lower surface to contact and applanate the cornea;
    an elongate blade extending along a longitudinal axis, the elongate blade comprising a cutting edge surface at a distal end of the blade, the cutting edge surface extending in a direction transverse to the longitudinal axis and having a cross-sectional radius less than about one micrometer; and
    a blade holder shaped to receive and hold the blade with the cutting edge surface extending along the lower surface of the applanator with a distance extending between the applanator and the cutting edge surface, the blade holder coupled to the cutting head to hold the elongate blade at an orientation so as to control a separation force and separate a viable layer of epithelium from the Bowman's membrane and form the pocket, wherein the distance from the lower surface of the applanator to the cutting edge surface of the blade is substantially greater than the thickness of the epithelium so as to separate the viable layer of epithelium from the underlying Bowman's membrane.

2. The system of claim 1, wherein the blade is oriented at an angle of about 0° from a straight line extending along a longitudinal guidance path of the blade.

3. The system of claim 1, wherein the blade has a maximum width substantially equal to the length of the cutting edge surface.

4. The system of claim 1, wherein the blade has a maximum width at the distal end of the blade and a second width at a more proximal location that is less than the maximum width.

5. The system of claim 1, wherein the blade is configured to be transversely oscillated, and has a distal portion that has a width effective in forming a corneal epithelial pocket comprising first and second lateral epithelial pocket edges at Bowman's membrane during transverse oscillation of the blade, and an adjacent proximal portion that has a proximal portion width effective in preventing contact of the proximal portion with the first or second lateral epithelial pocket edges during transverse oscillation of the blade.

6. The system of claim 1, wherein the blade holder is configured to oscillate the blade transversely to the longitudinal axis, and the applanator has a width that is greater than a maximum transverse dimension of the distal end of the blade during transverse oscillation of the blade.

7. The system of claim 1, wherein the distance from the lower surface of the applanator to the cutting edge surface is least about 190 micrometers.

8. The system of claim 1, further comprising a removable blade holder in contact with the blade and removable from the cutting head.

9. The system of claim 8, wherein the blade holder is a spring loaded blade holder.

10. The system of claim 8, wherein the blade holder is formed from a resilient material providing a biasing force effective in controlling movement of the blade during formation of a corneal epithelial pocket.

11. The system of claim 8, further comprising a motor engageable with the blade holder to cause oscillation of the blade.

12. The system of claim 1, further comprising a suction ring that comprises a cornea contacting portion and a spaced apart cutting head guidance portion, and the blade cutting edge surface is located between the cornea contacting portion and the cutting head guidance portion during formation of the corneal epithelial pocket.

13. The system of claim 1, wherein the cross-sectional radius is within a range from about 300 nanometers to about 800 nanometers.

14. A corneal epithelial pocket formation system for forming a pocket in a cornea of an eye, the cornea having a Bowman's membrane and an epithelium disposed over the Bowman's membrane, the epithelium having a thickness of approximately 50 to 55 micrometers, the system, comprising:
    a suction ring comprising a cornea contacting portion and a spaced apart cutting head guidance portion;
    a cutting head in contact with the cutting head guidance portion of the suction ring, the cutting head comprising,
        an applanator having a lower surface to contact and applanate an area on the cornea having a dimension across,
        a spring loaded blade holder coupled to the applanator, and
        an elongate blade extending along a longitudinal axis from the spring loaded blade holder at an angle of about 0° from a straight line extending along a longitudinal guidance path of the blade to separate a viable layer of epithelium from the Bowman's membrane and form a pocket, the blade having a distal end portion that comprises a cutting edge surface defining a maximum width of the blade, and a proximal portion defining a width less than the distal end portion, the proximal portion and the distal end portion extending along the longitudinal guidance path to control an orientation the cutting edge surface and a separation force so as to separate the corneal epithelium from the underlying Bowman's membrane when the head is advanced along the guidance portion of the suction ring, wherein the cutting edge surface has a cross-sectional radius within a range from about 300 nanometers to about 800 nanometers and wherein the lower surface of the applanator is separated from the cutting edge surface of the blade with a distance of at least about 160 micrometers to pass the viable layer of epithelium between the applanator and the cutting edge surface when the cutting head is advanced along the guidance portion of the suction ring; and a housing comprising a first motor coupled to the blade holder to advance the blade along the longitudinal axis and a second motor coupled to the blade holder to oscillate the blade with a movement of the blade transverse to the longitudinal axis, wherein the movement transverse to the longitudinal axis is sized to form an epithelial pocket having a transverse dimension less than the dimension across the applanation area.

15. A package for forming a pocket in a cornea of an eye, the cornea having a Bowman's membrane and an epithelium over the Bowman's membrane, the epithelium having a thickness of approximately 50 to 55 micrometers, the package comprising:

a blade, the blade comprising a cutting edge surface having a cross-sectional radius from about 300 nanometers to about 800 nanometers;

a spring loaded blade holder engageable with a cutting head of a motorized device and removable from the cutting head of the motorized device, the blade holder being structured to retain the corneal epithelial pocket forming blade at an orientation to control a separation force and separate a viable layer of epithelium from the Bowman's membrane and form the pocket when the blade holder is engaged with the cutting head; and an applanator having a lower surface to contact and applanate the cornea, wherein the lower surface of the applanator is separated from the cutting edge surface of the blade with a distance of at least about 160 micrometers when the blade is positioned in the spring loaded blade holder to separate the viable epithelial layer from the Bowman's membrane.

16. The package of claim 15, wherein the blade comprises a sterilized blade and the spring loaded blade holder comprises a sterilized spring loaded blade holder.

17. A blade for for forming a pocket in a cornea of an eye, the cornea having a Bowman's membrane and an epithelium under the Bowman's membrane, the epithelium having a thickness of approximately 50 to 55 micrometers, the blade comprising:

a distal end portion and proximal portion; and a cutting edge surface located at a distal end of the blade, the cutting edge surface having a cross-sectional radius from about 300 nanometers to about 800 nanometers, wherein the blade extends along a longitudinal axis from the proximal portion to the distal end portion oriented to separate a viable layer of corneal epithelium of an eye of a patient from an underlying Bowman's membrane of the eye during formation of a corneal epithelial pocket with a separation fore, wherein the separation force is controlled a distance of at least about 160 micrometers from the cutting edge surface of the blade to a lower surface of an applanator, wherein the distance of at least about 160 micrometers is greater than the thickness of the epithelium, and wherein the adjacent proximal portion is located in the corneal epithelial pocket during formation thereof and has a width less than the width of the distal end portion.

* * * * *